(12) United States Patent
London

(10) Patent No.: US 10,945,662 B2
(45) Date of Patent: Mar. 16, 2021

(54) SMART FITNESS APPARATUS

(71) Applicant: Justin London, Chicago, IL (US)

(72) Inventor: Justin London, Chicago, IL (US)

(*) Notice: Subject to any disclaimer, the term of this patent is extended or adjusted under 35 U.S.C. 154(b) by 516 days.

(21) Appl. No.: 15/819,794

(22) Filed: Nov. 21, 2017

(65) Prior Publication Data

US 2018/0160975 A1   Jun. 14, 2018

Related U.S. Application Data

(60) Provisional application No. 62/448,851, filed on Jan. 20, 2017, provisional application No. 62/433,222, filed on Dec. 12, 2016.

(51) Int. Cl.

| A43B 3/00 | (2006.01) |
|---|---|
| A61B 5/00 | (2006.01) |
| A43B 13/20 | (2006.01) |
| A61B 5/0205 | (2006.01) |
| A61B 5/103 | (2006.01) |
| A61B 5/11 | (2006.01) |

(Continued)

(52) U.S. Cl.
CPC ............ *A61B 5/6807* (2013.01); *A43B 3/001* (2013.01); *A43B 3/0005* (2013.01); *A43B 3/0021* (2013.01); *A43B 3/0078* (2013.01); *A43B 13/20* (2013.01); *A61B 5/00* (2013.01); *A61B 5/0004* (2013.01); *A61B 5/0205* (2013.01); *A61B 5/02055* (2013.01); *A61B 5/1036* (2013.01); *A61B 5/1118* (2013.01); *A61B 5/021* (2013.01); *A61B 5/02438* (2013.01); *A61B 5/1112* (2013.01)

(58) Field of Classification Search
CPC ........ A43B 3/0005; A61B 5/6807; A61B 5/00

USPC .......................................................... 36/137
See application file for complete search history.

(56) References Cited

U.S. PATENT DOCUMENTS 5,452,269 A   9/1995   Cherdak
5,457,900 A   10/1995   Roy
(Continued)

FOREIGN PATENT DOCUMENTS

CN   204120323 U   1/2015
CN   204120325 U   1/2015
(Continued)

OTHER PUBLICATIONS

Wenling Rechargeable USB Led Micro Led String Shoes Lights; printed Apr. 27, 2015 from website www.alibaba.com/product-detail/wenling-rechargeable-USB-led-micro-led_60081394111.html?s=p; 10 pages.

*Primary Examiner* — Timothy K Trieu
(74) *Attorney, Agent, or Firm* — Thomas E. Lees, LLC

(57) ABSTRACT

In one embodiment, a shoe includes a top portion configured to provide covering to a top of a user's foot, a sole portion coupled to the top portion, and one or more processors embedded within the sole portion. Communicatively coupled to the one or more processors are one or more memory modules, one or more user input devices, and a user output device. The user input device includes at least a microphone. Machine readable instructions stored in the one or more memory modules, when executed by the one or more processors, cause the shoe to: receive a command from a user with the one or more user input devices; process the command from the user; and output information with the user output device relevant to the command from the user.

8 Claims, 9 Drawing Sheets

(51) Int. Cl.
 *A61B 5/021* (2006.01)
 *A61B 5/024* (2006.01)

(56) References Cited

U.S. PATENT DOCUMENTS

| | | | |
|---|---|---|---|
| 5,471,405 A | 11/1995 | Marsh | |
| 6,434,485 B1 | 8/2002 | Beason et al. | |
| 7,607,243 B2 * | 10/2009 | Berner, Jr. | A43B 3/0005 36/136 |
| 8,421,822 B2 * | 4/2013 | Odland | A43B 1/0027 345/619 |
| 8,641,220 B1 | 2/2014 | Lin | |
| 2004/0103563 A1 * | 6/2004 | Linge | A43B 3/001 36/137 |
| 2007/0011919 A1 | 1/2007 | Case | |
| 2011/0131839 A1 * | 6/2011 | Ballin | A43B 13/186 36/141 |
| 2011/0308113 A1 | 12/2011 | Hartford et al. | |
| 2014/0157632 A1 | 6/2014 | Kim | |
| 2015/0181314 A1 * | 6/2015 | Swanson | H04Q 9/00 340/870.07 |
| 2016/0338441 A1 | 11/2016 | London | |

FOREIGN PATENT DOCUMENTS

| | | |
|---|---|---|
| CN | 204191690 U | 3/2015 |
| JP | 3196251 U | 2/2015 |

\* cited by examiner

SMART FITNESS APPARATUS

CROSS-REFERENCE TO RELATED APPLICATIONS

This application claims the benefit of U.S. Provisional Application No. 62/433,222, entitled "Smart Shoes: Voice Activated Shoes with LFG Display and Navigation," filed Dec. 12, 2016, the entirety of which is hereby incorporated by reference, and U.S. Provisional Application No. 62/448,851, entitled "Smart Fitness Shoe and Apparel Monitoring and Tracking," filed Jan. 20, 2017, the entirety of which is hereby incorporated by reference.

TECHNICAL FIELD

The present specification generally relates to fitness apparatuses and, more specifically, to fitness apparatuses embodied in shoes and apparel that are able to track user usage and provide information to a user.

BACKGROUND

Fitness tracking devices allow a user to track their activity throughout the day. Some fitness tracking devices include GPS or other information that may be provided to the user. These fitness trackers are generally incorporated into devices that must be carried by the user. For example, many fitness trackers are incorporated into watches or bracelets that the user can wear. However, some athletes prefer not to have to carry or wear additional equipment while exercising.

Accordingly, a need exists for alternative fitness apparatuses that can be embodied in articles already worn by an athlete (e.g., shoes and apparel) that are able track a user's activities as well as provide desired information to the user.

SUMMARY

In one embodiment, a shoe includes a top portion configured to provide covering to a top of a user's foot, a sole portion coupled to the top portion, and one or more processors embedded within the sole portion. Communicatively coupled to the one or more processors are one or more memory modules, one or more user input devices, and a user output device. The user input device includes at least a microphone. Machine readable instructions stored in the one or more memory modules, when executed by the one or more processors, cause the shoe to: receive a command from a user with the one or more user input devices; process the command from the user; and output information with the user output device relevant to the command from the user.

In another embodiment, a shoe that includes a top portion configured to provide covering to a top of a user's foot, a sole portion coupled to the top portion, and one or more processors embedded within the sole portion. Communicatively coupled to the one or more processors are one or more pressure sensors, a pneumatic adjustment system, and one or more memory modules. The one or more pressure sensors are configured to output a pressure signal indicative of a pressure applied by the user's foot to a portion of the sole portion. The pneumatic adjustment system is operable to adjust a cushioning of the sole portion. Machine readable instructions stored in the one or more memory modules, when executed by the one or more processors, cause the shoe to: determine a pressure applied by the user's foot to the portion of the sole portion based on the pressure signal from the one or more pressure sensors, determine a pressure applied by the user's foot to the portion of the sole portion base on the pressure signal from the one or more pressure sensors, calculate a cushioning adjustment, and adjust the cushioning of the sole portion with the pneumatic adjustment system.

In yet another embodiment, a fitness apparatus includes an apparel item, one or more processors coupled to the apparel item and one or more processors coupled to the apparel item. Communicatively coupled to the one or more processors are one or more memory modules, one or more user input devices, and a user output device. Machine readable instructions stored in the one or more memory modules, when executed by the one or more processors, cause the fitness apparatus to: receive a command from a user with the one or more user input devices; process the command from the user; and output information with the user output device relevant to the command from the user.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
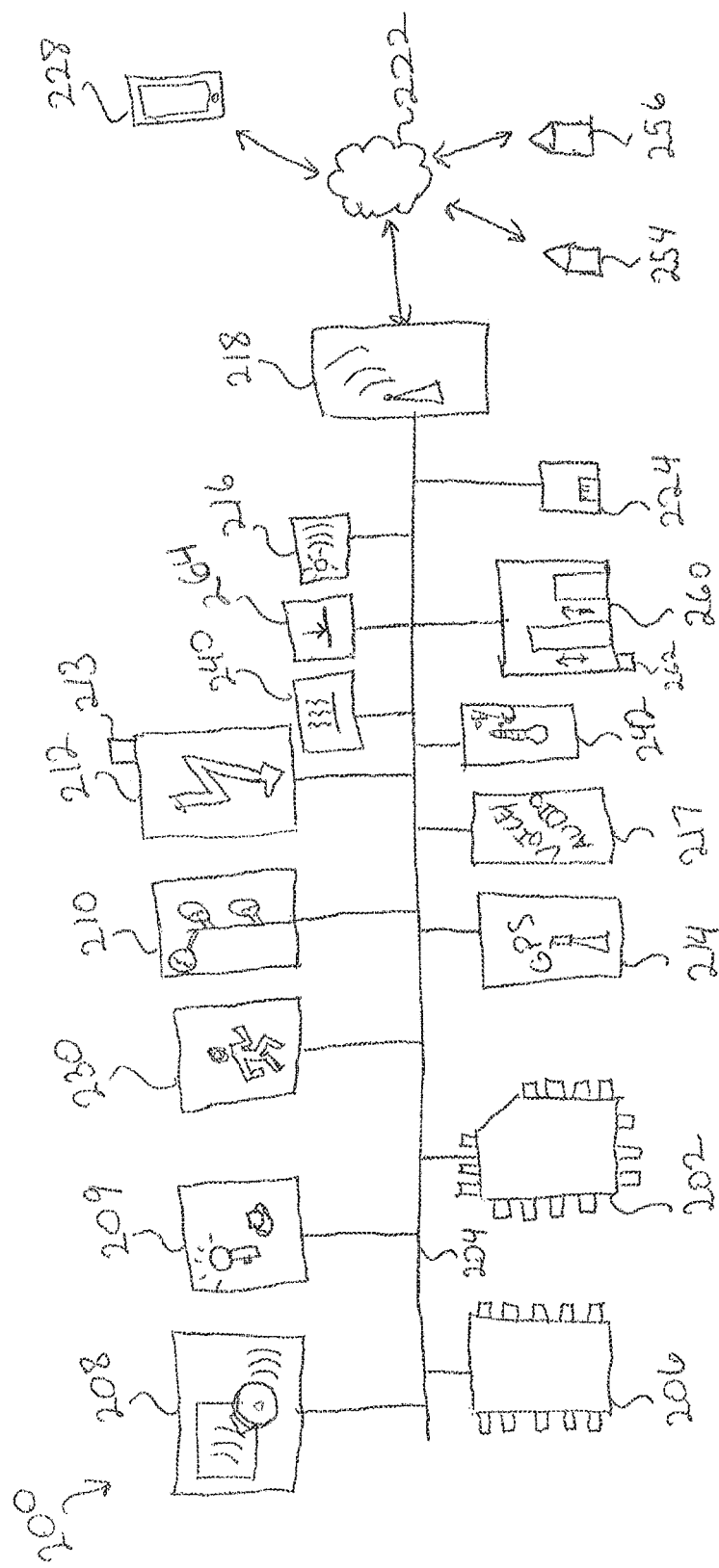
FIG. 1 schematically depicts a fitness apparatus, according to one or more embodiments shown and described herein.

Reference will now be made in detail to embodiments of the fitness apparatus described herein, examples of which are illustrated in the accompanying drawings. Whenever possible, the same reference numerals will be used throughout the drawings to refer to the same or like parts. Referring to the figures generally, embodiments of the fitness apparatus provided herein are directed to a fitness apparatus as embodied in a shoe and/or other apparel pieces (e.g., tops, bottoms, and the like). In at least one embodiment, a shoe is configured with technology so as to be able to receive an instruction from a user or mobile device, determine the information requested by the user or mobile device, and output information relevant to the user's instruction through a user output device (e.g., display, speaker, and the like). For example, a shoe with a GPS chip built therein, may receive an instruction from a user to determine a route for the user or display the route and position of the user on a mobile device, (e.g., a parent may track their child from their mobile phone). The shoe may be able to respond to the user by providing navigation guidance through a computerized voice produced through speaker's built in to the shoe or that can be heard in a user's wireless Bluetooth headset. In some embodiments, the fitness apparatus may include various activity sensors that are operable to measure fitness information (e.g., distance traveled, cadence, steps taken, heart rate, speed, calories burned, and the like). Upon request, the fitness apparatus can display or otherwise present the fitness information to the user on a display. Additionally, the fitness apparatus as described herein can include a plurality of lighting elements coupled to the shoe. The plurality of lighting elements may be configured to operate in various lighting modes and emit different colors, which may also provide information to the user. In yet further embodiments, the fitness apparatus, as embodied in a shoe, includes a pneumatic adjustment system that can automatically adjust the cushioning support within a sole portion of the shoe in response to a user's movement. These and additional embodiments will be described in greater detail below with reference to the corresponding figures.

While embodiments of the fitness apparatus are described herein specifically with respect to a shoe, the fitness apparatus may be embodied in other apparel or other daily use items such as handbags, backpacks, keys or key chains, eye wear, and the like. Furthermore, in some embodiments, the fitness apparatus as described herein, may be embodied or distributed across in multiple shoes, other apparel, and accessories simultaneously. In addition to the various fitness tracking capabilities of the fitness apparatus, the fitness apparatus as embodied in apparel or accessories may also be used without such capabilities for solely aesthetic or fashionable reasons.

Referring specifically to FIG. 1, a schematic layout of the fitness apparatus 200 is generally depicted. In particular, the fitness apparatus 200 as illustrated includes one or more processors 202, one or more memory modules 206, a communication path 204, network interface hardware 218, one or more user input devices 208, one or more output devices 209, one or more activity sensors 230, one or more lighting elements 210, a light sensor 216, a GPS chip 214, a voice/audio chip 217, one or more power supplies 212, one or more temperature sensors 242, one or more heating elements 240, a charging port 224, one or more pressure sensors 264, and a pneumatic adjustment system 260. While various components are shown, it will be understood that a greater or fewer number of components may be included without departing from the scope of the present disclosure. As will be described herein, the various components of the fitness apparatus 200 may be imbedded in an article or may be coupled to multiple or different articles.

FIGS. 2-7 generally illustrate an example embodiment of the fitness apparatus 200 as embodied in a shoe 100. The shoe 100 includes a top portion 102, a sole portion 104, an interior portion 106, and a tongue portion 110. As will be described in more detail herein, the various components of the fitness apparatus 200 that allow a user to interact with the shoe 100 are coupled to the shoe 100. While the shoe 100 shown in FIGS. 2-7 is a sneaker, the shoe 100 may be a heeled shoe, a platform shoe, a sandal, a boot, a flip flop or the like. Additionally, the shoe 100 may be a women's shoe, a men's shoe, or a child's shoe. The top portion (uppers) 102 of the shoe 100 is configured to provide a covering for the top of a user's foot (e.g., a human foot).

As noted above, the shoe 100 includes the sole portion 104 placed beneath the top portion 102. In embodiments, the sole portion 104 is attached to the top portion 102 by using an adhesive, stitching the two portions together, or the like. In embodiments, the sole portion 104, or only a portion thereof, may be made of a material like plastic, synthetic, polymer, resin, foam, hybrid foam, gel, phylon, ethylene-vinyl acetate (EVA), or a combination thereof. In some embodiments, the sole portion 104 may be transparent, translucent, or only partially transparent or translucent. The interior portion 106 of the shoe 100 lines the top portion 102 and is in direct contact with the human foot, once placed into the shoe 100.

The sole portion 104 may contain memory foam cushioning for optimal foot support and comfort. Such foam (or synthetic foam) may also be used in lining the top portion 102 of the shoe 100 to provide additional comfort and cushioning. The foam or other cushioning could also provide protection for wiring and electronic components from external impact forces. For example, FIG. 5 illustrates a portion of the sole portion 104 as made from durable memory foam/polymer insulation 111. The durable memory foam/polymer insulation 111 securely surrounds and protects the electronic components so that they remain firmly intact and secured regardless of movement of the shoe 100. In some embodiments, a highly durable protective layering/translucent plastic coating may surround the cabling/wiring running in between the outside and inside of the shoe 100 and the sole portion so that the variously components (in particular the LFG display 150 shown in FIG. 4 and as will be described herein) are firmly secured and protected from forces to the side of the shoe 100 (e.g., a soccer ball that hits the side).

Figure 5:
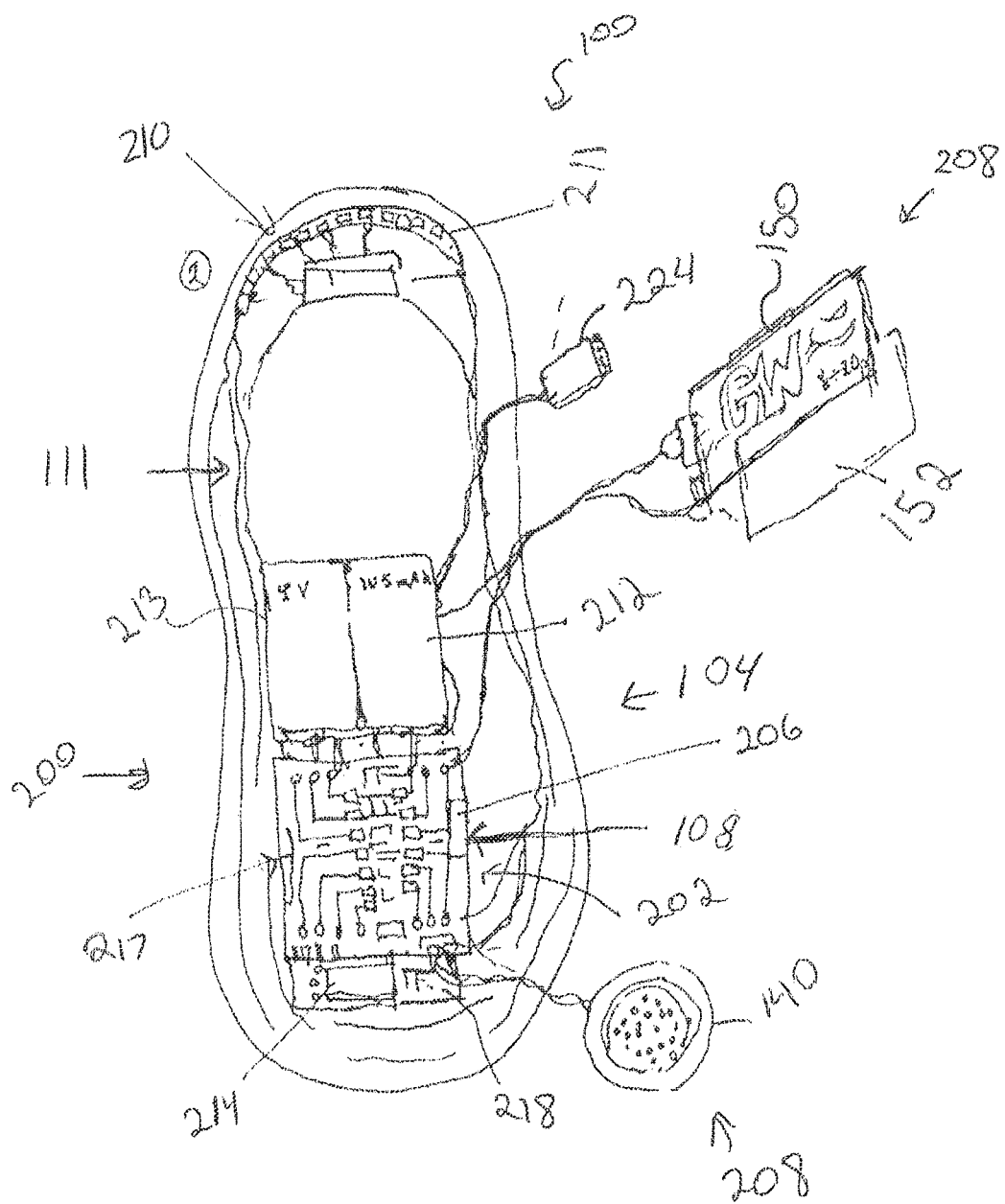
FIG. 5 illustrates a portion of the various components shown in FIG. 1 fitted with a sole portion of the shoe of FIG. 2, according to one or more embodiments shown and described herein.
Figure 6:
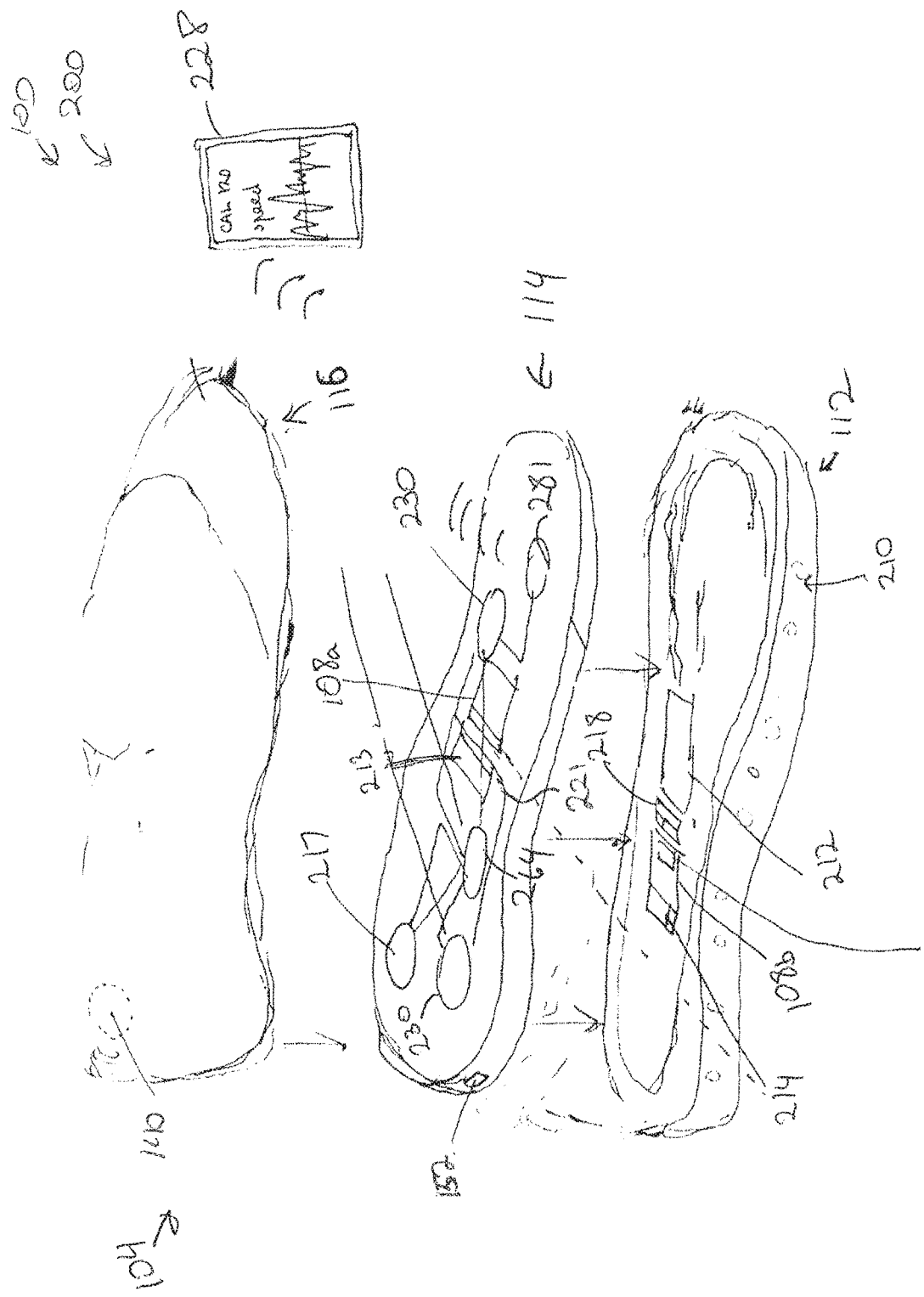
FIG. 6 illustrates a partially exploded view of the shoe of FIG. 2, according to one or more embodiments shown and described herein.
Figure 7:
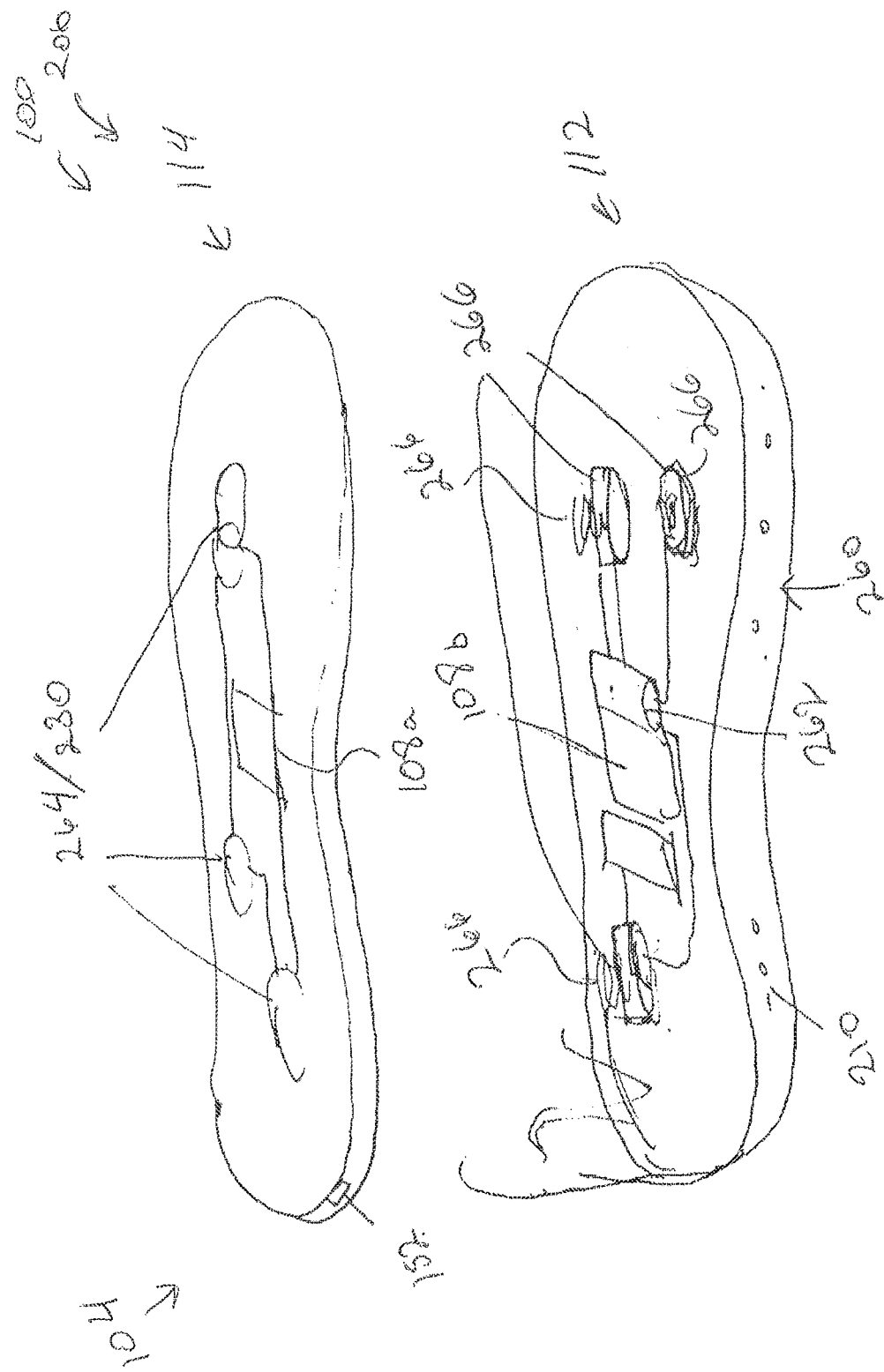
FIG. 7 illustrates a pneumatic adjustment system within a sole portion of a shoe of FIG. 2, according to one or more embodiments shown and described herein.

Referring specifically to FIGS. 6 and 7, the sole portion 104 includes a bottom sole portion (consisting of midsole and outsole) 112, an inner sole portion 114, and an upper sole portion 116. In some embodiments, there may only be an inner sole portion 114 and a bottom sole portion 112. In some embodiments, the inner sole portion 114 can be removable from the shoe 100. Each of the sole portions 112, 114, and 116 may or may not incorporate one or more components of the fitness apparatus 200 described herein. For example, one or more of the sole portions 112, 114, and 116 can include a printed circuit board 108 onto which at least some of the various components are mounted. In embodiments, the printed circuit board 108 includes the one or more processors 202 and the one or more memory modules 206, the power supply 212, the satellite antenna 230, the GPS chip 214, audio/voice chip 217, the pneumatic adjustment system 260, in addition to the other components (not shown) and depicted in FIG. 2. It is noted while FIGS. 5-7 generally illustrate example layouts of the various components of the fitness apparatus 200 incorporated into the shoe 100, one of skill in the art would recognize that the presently illustrated layout may be rearranged without departing from the scope of the present disclosure.

Figure 2:
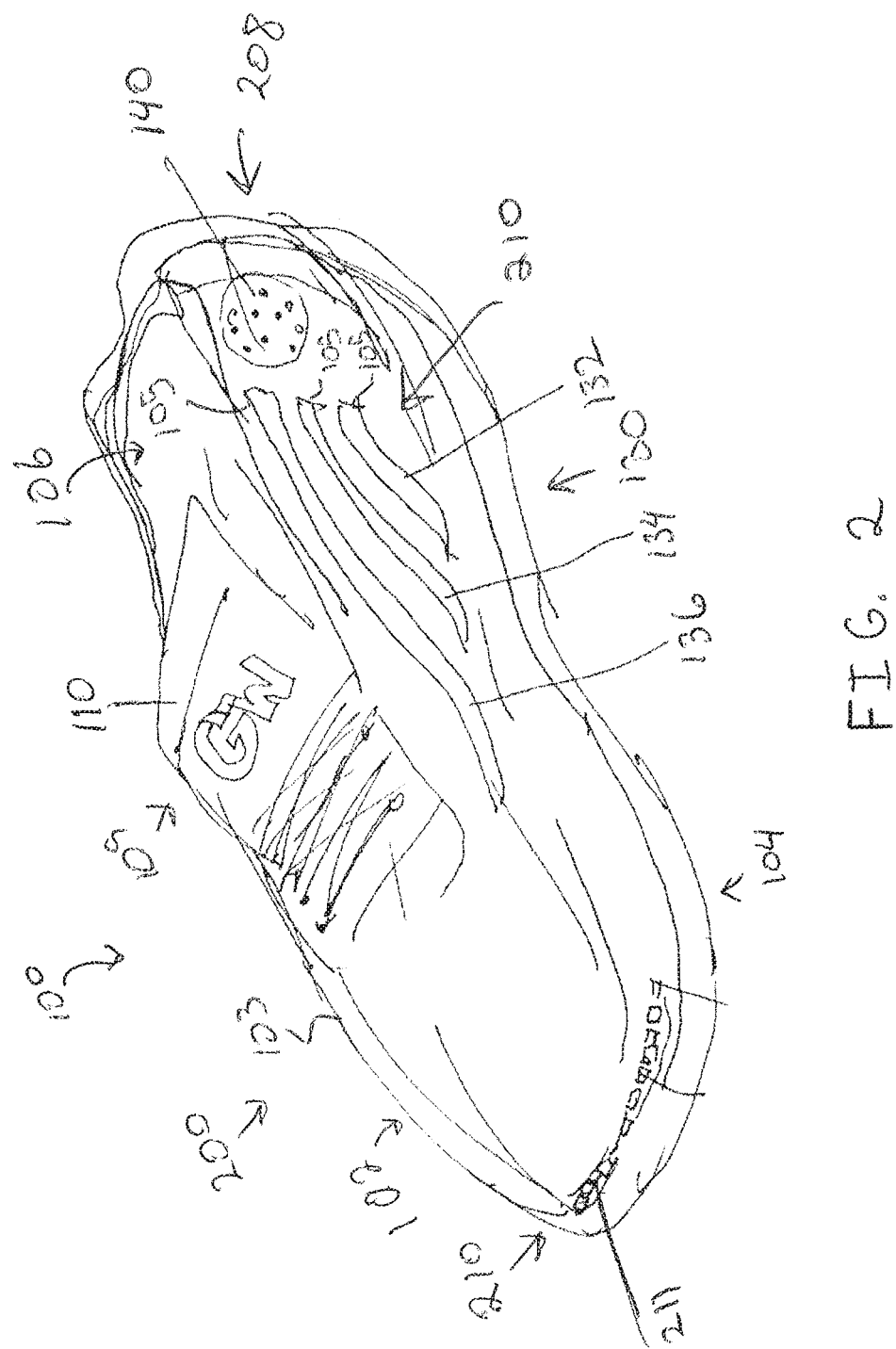
FIG. 2 depicts the fitness apparatus of FIG. 1 embodied in a shoe, according to one or more embodiments shown and described herein.
Figure 3:
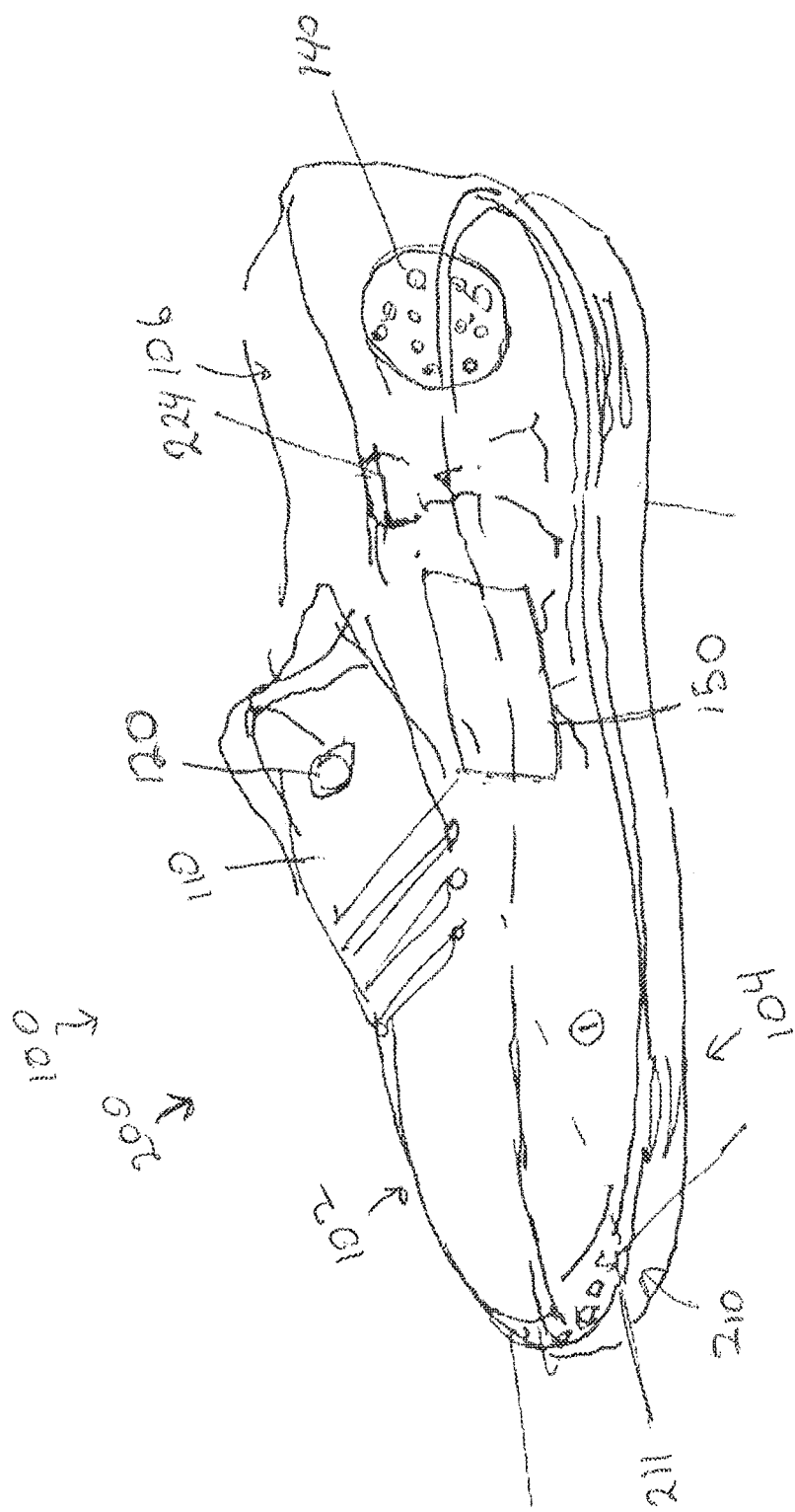
FIG. 3 depicts, a side view of the shoe of FIG. 2, according to one or more embodiments shown and described herein.
Figure 4:
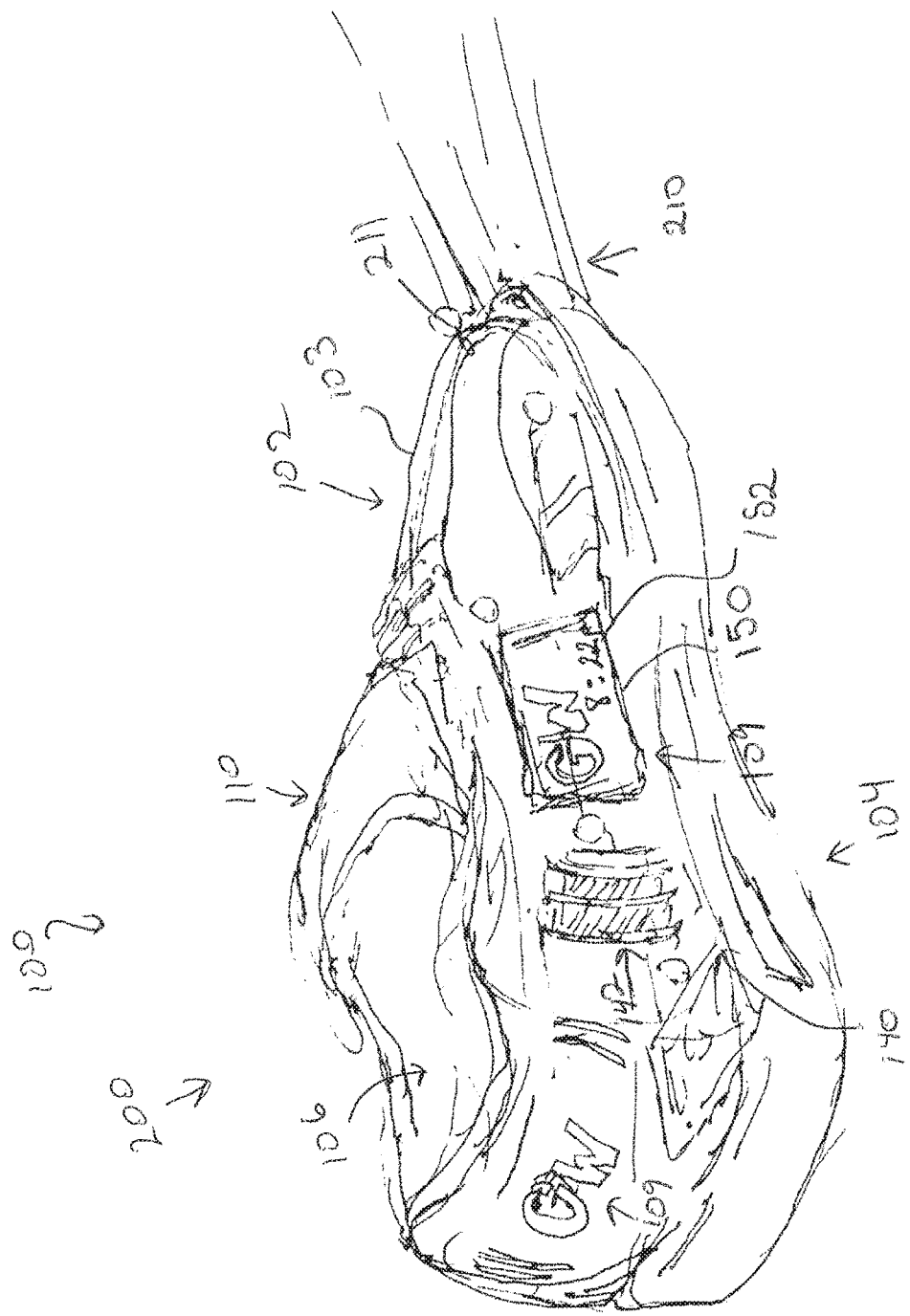
FIG. 4 depicts a rear perspective view of the shoe of FIG. 1, according to one or more embodiments shown and described herein.

Referring to FIGS. 2-4, the shoe 100 may also include at least one logo portion 109 that accommodates a logo 109 or brand of the shoe 100 on an exterior of the top portion 102 of the shoe 100. In some embodiments, there may be more than one logo portion 109. As will be described in greater detail herein, in some embodiments, the at least one logo portion 109 may be part of the one or more user output devices 208. For example, the at least one logo portion 109 may be illuminated and/or be a dynamically changing display (e.g., LFG display 150) configured to output information relevant to a user request.

Referring again to FIG. 1, the communication path 204 may be formed from any medium that is capable of transmitting a signal such as, for example, conductive wires, conductive traces, optical waveguides, or the like. Moreover, the communication path 204 may be formed from a combination of mediums capable of transmitting signals. In one embodiment, the communication path 204 comprises a combination of conductive traces, conductive wires, connectors, and buses that cooperate to permit the transmission of electrical data signals to components such as processors 202, memories, sensors, input devices, output devices 209, and communication devices. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium. The communication path 204 communicatively couples the various components of the fitness apparatus 200. As used herein, the term "communicatively coupled" means that coupled components are capable of exchanging data signals with one another such as, for example, electrical signals via conductive medium, electromagnetic signals via air, optical signals via optical waveguides, and the like.

As noted above, the fitness apparatus 200 includes the one or more processors 202. Each of the one or more processors 202 may be any device capable of executing machine readable instructions. Accordingly, each of the one or more processors 202 may be a controller, an integrated circuit, a microchip, a computer, or any other computing device. The one or more processors 202 are communicatively coupled to the other components of the fitness apparatus 200 by the communication path 204. Accordingly, the communication path 204 may communicatively couple any number of processors 202 with one another, and allow the modules coupled to the communication path 204 to operate in a distributed computing environment. Specifically, each of the modules may operate as a node that may send and/or receive data. The one or more processors 202 can be coupled to the printed circuit board 108 within the sole portion 104 of the shoe 100 such as shown in FIG. 5. Referring to FIG. 6, the there may be multiple printed circuit boards 108a such that a first printed circuit board 108a is located within the inner sole 114 and a second printed circuit board 108b is located within a cavity of the bottom sole 112. The one or more processors 220 can be coupled to one or more of the printed circuit boards 108a, 108b.

As noted above, the fitness apparatus 200 includes the one or more memory modules 206. Each of the one or more memory modules 206 of the fitness apparatus 200 is coupled to the communication path 204 and communicatively coupled to the one or more processors 202. The one or more memory modules 206 may comprise RAM, ROM, flash memories, hard drives, or any device capable of storing machine readable instructions such that the machine readable instructions can be accessed and executed by the one or more processors 202. The machine readable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable instructions and stored on the one or more memory modules 206. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. The one or more memory modules 206 may include program embedded software that enables a user to select or enter a request for information (e.g., direction, fitness stats, and the like) and output that information to a user output device (e.g., speakers, displays, remote devices, and the like). The one or more memory modules 206 can be coupled to the printed circuit board 108 within the sole portion 104 of the shoe 100, as shown in FIGS. 5-7.

In some embodiments, the one or more memory modules 206 include speech recognition software (e.g., AVIA) for allowing the one or more processors 202 to recognize vocalized commands from a user and determine a meaning of the command so that a responsive output can be provided by the fitness apparatus 200. For example, and as will be described in greater detail herein, the fitness apparatus 200 include one or more user input devices 208 such as a microphone for receiving vocalized commands from a user. As will be described in greater detail herein vocalized commands may include any number of requests including, but not limited to, "play music," "turn on lighting mode (insert particular lighting mode)," "directions to (insert particular location)," "distance to destination," "calories burned," "distance traveled," "steps taken," "heart rate," etc.

In some embodiments, the one or more memory modules 206 includes one or more RFID decoder algorithms, such as an automatic RFID code recognition engine that processes RFID input signals received from the RFID scanner and/or extracts information from such signals, as will be described in further detail below. Furthermore, the one or more memory modules 206 include machine readable instructions that, when executed by the one or more processors 202, cause the fitness apparatus 200 to perform the actions described below.

In some embodiments, the one or more memory modules 206 may include a portable memory device such as a removable memory chip, USB drive, or SIM card, such that information stored on the one or more memory modules 206 can be transferred from the fitness apparatus 200 to a remote device 228. For example, where the fitness apparatus 200 is incorporated into a shoe 100 or other apparel, a slot 152 (illustrated in FIGS. 6 and 7) could be provided to be able to insert or remove the portable memory device which could be directly connected by USB, for example, to a laptop to access the data stored on the portable memory device. For example, the shoe 100 could be provided with the slot 152 on the back or sole portion 104 of the shoe 100 such that the portable memory component could be inserted or removed from the shoe 100. Referring to FIGS. 6 and 7, a slot 152 may be a USB port provided in the inner sole portion 114 for recharging and receiving power from USB cables and/or transmitting data to and/or from a USB flash drive. As noted above, the inner sole portion 114 may be removable to allow access to the slot 152. In some cases, the slot 152 may be accessible from an exterior of the shoe 100, such as at the back or heel of the shoe 100.

Referring again to FIG. 1, as noted above, the fitness apparatus 200 includes network interface hardware 218 for communicatively coupling the fitness apparatus 200 and a network 222. The network interface hardware 218 is coupled to the communication path 204 such that the communication path 204 communicatively couples the network interface hardware 218 to other modules of the fitness apparatus 200. The network interface hardware 218 can be any device capable of transmitting and/or receiving data via a wireless or cellular network 222. Accordingly, the network interface hardware 218 can include a communication transceiver for sending and/or receiving data according to any wireless communication standard. For example, the network interface hardware 218 may include a chipset (e.g., antenna (e.g., F-inverted type), processors 202, machine readable instructions, etc.) to communicate over wireless computer networks such as, for example, wireless fidelity (WiFi), WiMax, Bluetooth, IrDA, Wireless USB, Z-Wave, ZigBee, or the like. In some embodiments, the network interface hardware 218 includes a Bluetooth transceiver that enables the fitness apparatus 200 to exchange information between a remote device 228 (e.g., a smartphone, a smartwatch, a Bluetooth headset, a computer monitor, a laptop, a tablet, or the like) via Bluetooth communication. Accordingly the network interface hardware 218 can include one or more of the following chips imbedded in the printed circuit board 108: RFID chips, the Bluetooth® chips, the WiFi chips, and the like For example, data from the remote device 228 may be provided to the fitness apparatus 200 via the network interface hardware 218. Specifically, the fitness apparatus 200 may include an F-inverted type antenna for communicating over one or more of the wireless computer networks described above. Moreover, the fitness apparatus 200 may include a mobile antenna for communicating with the network 222. Accordingly, the antenna may be configured to send and receive data according to a mobile telecommunication standard of any generation (e.g., 1G, 2G, 3G, 4G, 5G, etc.).

In some embodiments, the remote device 228 may also have one or more memory modules, and one or more processors. Further, the remote device 228 may also have a tactile input hardware integrated with the remote device 228. In some embodiments, the remote device 228 includes a display and the display may be a touchscreen. In some embodiments, a user may use to the remote device 228 to input settings (e.g., a lighting mode, fitness goals, navigation requests, and the like) into the fitness apparatus 200. For example, an app downloaded on the remote device 228 may allow a user to easily share information between the fitness apparatus 200 and the remote device 228. For example, the remote device 228 can transfer music files, trip data, mapping software updates via the network interface hardware 218 to and from the fitness apparatus 200. In embodiments, the remote device 228 is also used to receive fitness data sent through the network interface hardware 218 and display the information received. Fitness data includes information indicative of the distance traveled, the calories burned, revolutions when cycling, average speed, distance to destination, current location and the like.

In embodiments, more than one remote device 228 may be communicatively coupled with the fitness apparatus 200. In this instance, fitness apparatus 200 may be configured to send fitness data to some or all of the remote devices 228. For example, the fitness apparatus 200 when worn by a child user, may be configured to send fitness data related to the current position of the child wearing the fitness apparatus 200 coupled to the child's remote device 228 and a parent user's remote device 228. Such embodiments, and as will be described in greater detail herein, can allow a parent to track a location of their child in real-time and determine if a child is outside of a predetermined area. This can help prevent a child from becoming lost.

Referring to FIG. 1, the network 222 generally includes one or more computing devices configured to receive and transmit data according to a network 222 communication protocol. In some embodiments, the network 222 includes a wired system such as public switched telephone network (PSTN) or a backhaul networks. In some embodiments, the network 222 includes one or more of a wide area network, a metropolitan area network, the Internet, a satellite network, or the like. Further example networks include but are not limited to GSM, GPRS, and WCDMA. Thus, the network 222 generally includes one or more antennas, transceivers, and processors 202 that execute machine readable instructions to exchange data over various wired and/or wireless networks.

In some embodiments, the network 222 can be utilized as a wireless access point by the fitness apparatus 200 to access one or more servers (e.g., a first server 254 and/or a second server 256). The first server 254 and second server 256 generally include processors, memory, and chipset for delivering resources via the network 222. Resources can include providing, for example, processing, storage, software, and information from the first server 254 and/or the second server 256 to the fitness apparatus 200 via the network 222. Additionally, it is noted that the first server 254 or the second server 256 can share resources with one another over the network 222 such as, for example, via the wired portion of the network 222, the wireless portion of the network 222, or combinations thereof.

Still referring to FIG. 1, the one or more servers accessible by the fitness apparatus 200 via the network 222 may include third party servers that provide additional capability for performing the functionality described herein. For example, the first server 254 and/or the second server 256 may store the location coordinates (on a GPS map) related to the start position, the end position, the distance traveled, and the route traveled in a database for retrieval by the fitness apparatus 200. It should be understood that the fitness apparatus 200 and/or the remote device 228 may be communicatively coupled to any number of servers by way of the network 222. In some embodiments the fitness apparatus 200 can communicate with mapping software on a third party server including Google Maps or Google Satellite.

As noted above, the fitness apparatus 200 includes a GPS chip 214 communicatively coupled to the one or more processors 202. By way of example, the GPS chip 214 could utilize a SIM968 module which is a compact Quad-Bank GSM/GPRS-enable module base on a PNX4851 platform also equipped with GNSS technology for satellite navigation. The complete design in a SMT type chip makes it easy to integrate GSM/GPRS&GPS as an all-in-one-solution. It is programmed by a SIM application toolkit and utilizes a supply voltage range: V-BAT: 3.2V to 4.8V, V-GPS: 2.8V to 4.3V, VCHG: 5V.

The GPS chip 214 may include a satellite antenna and machine readable instructions in the one or more memory modules 206 that perform the GPS-related functions described herein when executed by the one or more processors 202. In embodiments, the GPS chip 214 is communicatively coupled to the one or more memory modules 206 and the one or processors 202. In embodiments, the fitness apparatus 200 is configured to obtain and update positional information of the user and provide route information to a user upon a request/command for information received over the one or more user input devices 208. For example, the fitness apparatus 200 may display such positional, mapping, and route information on a remote device display 228 or on a built-in display. The GPS chip 214 may be able to obtain and update positional information based on geographical coordinates, i.e. latitudes and longitudes, or via electronic positional information received through satellites. The GPS chip 214 may further allow the one or more processors 202 to calculate a route for a user and direct the user, using the one or more user input devices 208 along the route. Furthermore, in embodiments, machine readable instructions stored in the one or more memory modules 206 cause the fitness apparatus 200 to perform various fitness determination tasks when executed by the one or more processors 202.

In embodiments, the various fitness determination tasks include determining a start position and an end position. The start position may be a position at which the user begins to use the fitness apparatus 200. The end position may be a position at which a user has completed her use of the fitness apparatus 200. For example, the start position may be the geographical coordinates at which the user begins her workout and the end position may be the geographical coordinates at which the user ends her workout. In embodiments, the distance traveled between the start position and the end position is determined. The distance traveled may be measured in kilometers or miles, as per the user's preference. Another fitness determination task may include determining a route between the start position and a designated stop position as determined by the user. In embodiments, the route between the start and stop position may be displayed in the form of a map on a display as will be described in more detail herein. Further, the start position and the stop position may also be displayed on a map on the remote device 228. In embodiments, the fitness apparatus 200 (e.g. using the GPS chip 214) is configured to track movement information indicating how a user arrived at the end position from the start position. In embodiments, the fitness data determined above may be stored in the one or more memory modules 206 and transmitted with the network interface hardware 218, which may include an RFID chip, a Bluetooth chip and a Wifi chip, to be displayed on the remote device 228.

In some embodiments, the various fitness determination tasks also include determining a current position of the fitness apparatus 200. The current position may be the geographical coordinates at which the fitness apparatus 200 is located at a given time. Further, in embodiments, fitness determination tasks also include determining whether the current position is within a pre-determined radius from a reference position. When the fitness apparatus 200 is outside of the pre-determined radius from the reference position, the fitness apparatus 200 is configured to send, automatically the current position of the fitness apparatus 200 to a remote device 228 (e.g., smartphone, computer, and the like). For example, the fitness apparatus 200 can send a notification to a smartphone indicating that the fitness apparatus 200 is no longer within the pre-determined radius. In embodiments, the fitness apparatus 200 may be configured to set up a geofence boundary. This feature may be used for a parent to track the location of her child, and whether the child is within a pre-determined radius of a house, school, day care, and the like. When the child is outside of the predetermined radius an alert may be issued to the parent's remote device 228 (e.g., smartphone and the like). Further, the fitness apparatus 200 may also be configured to map the reference position and the current position on apps such as Google Maps or Google Earth. Accordingly, parents may be able to track and monitor their child in real-time, thereby reducing the possibility their child will become lost. In some embodiments, a friend, family member, or trainer's remote device may be given access to the location of the fitness apparatus.

In embodiments, fitness data related to the start position, the end position, the distance traveled between the start position and the end position, the current position, the reference position, and the route traveled is received by fitness apparatus 200 using the satellite antenna of the GPS chip 214. The satellite antenna is communicatively coupled to the communication path 204 such that the communication path 204 communicatively couples the satellite antenna to other modules of the fitness apparatus 200. The satellite antenna is configured to receive signals from GPS satellites. Specifically, in one embodiment, the satellite antenna includes one or more conductive elements that interact with electromagnetic signals transmitted by GPS satellites. The received signal is transformed into a data signal indicative of the location (e.g., latitude and longitude) of, for example, the start position or the end position, or the current position by the one or more processors 202. The data may then be stored on one of one or more memory modules 206 of the fitness apparatus 200.

As shown in FIG. 1, and as noted above, the fitness apparatus 200 includes one or more user input devices 210 coupled to the communication path 204 such that the communication path 204 communicatively couples the one or more user input devices 209 to other modules of the fitness apparatus 200. The one or more user input devices 209 may be any device capable of transforming mechanical, optical, audible, or electrical signals into a data signal capable of being transmitted with the communication path 204. Specifically, the one or more user input devices 209 may include any number of movable objects that transform physical motion into a data signal that can be transmitted over the communication path 204 such as, for example, a button, a switch, a knob, a microphone, or the like. In some embodiments, the one or more user input devices 208 may include the remote device 228 described above. The one or more user input devices 208 allow a user to input settings, commands, and the like into the fitness apparatus 200.

As noted herein the one or more user input devices 208 may include a microphone. The microphone can enable voice-control of the fitness apparatus 200. In this manner, a user can vocalize a request for information or other output from the fitness apparatus 200 using voice commands. In some embodiments, these commands can be vocalized through a Bluetooth headset worn by the user and/or through a built-in microphone. That is instructions stored on the one or more memory modules 206 can include speech recognition software which enables the one or more processors 202 to determine a request of the user and an appropriate response. In some embodiments, the microphone part of a combined speaker/microphone device capable of both receiving voice commands and emitting auditory messages/sounds. Example commands received from the user may include, but are not limited to, requests for fitness data (e.g., heart rate, speed, pace, distance traveled, steps taken), requests for navigation (e.g., "directions to library"), control of the one or more lighting elements 210 (e.g., lighting modes), and the like. In some embodiments, the user can turn the fitness apparatus 200 off and on by voice command. The microphone may be coupled to an amplifier and/or filter that amplifies the voice of the user while minimizing the impact of external background noise (e.g., wind, pedestrians, traffic, and the like). Additional types of user input devices 208 will be described below in reference to specific components.

Figure 8:
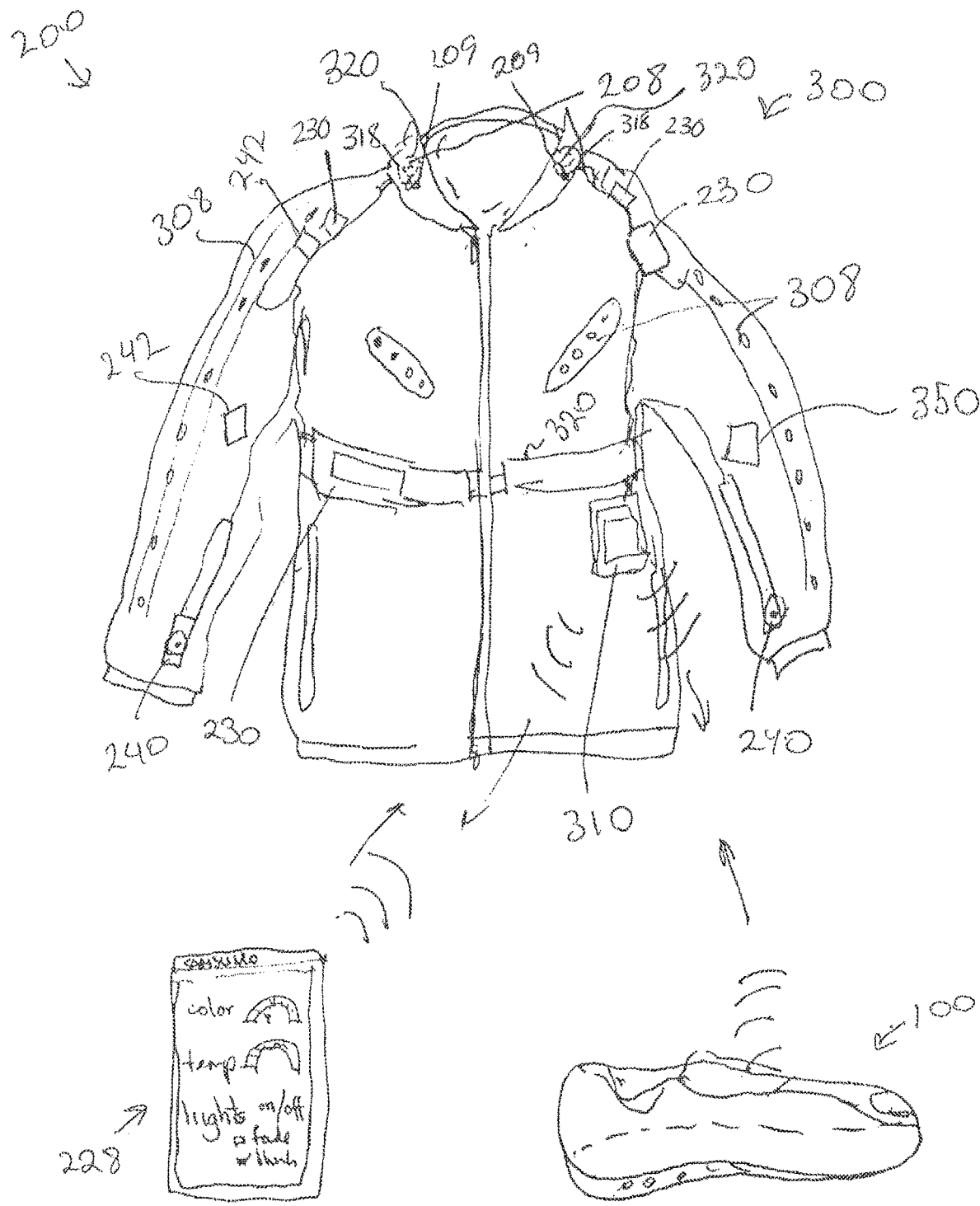
FIG. 8 illustrates the fitness apparatus of FIG. 1 distributed across various articles, according to one or more embodiments shown and described herein.

In the shoe embodiment, where a microphone is included as the one or more user output devices, the microphone may be incorporated in the sole portion 100 or coupled to the upper portion of the shoe 100. As noted above, the fitness apparatus may be incorporated into other articles. For example, FIG. 8 illustrates the fitness apparatus as at least partially incorporated into a jacket 300. Microphones 318 may be incorporated in a collar or hood of the jacket 300. When incorporated into the jacket 300, various components of the fitness apparatus 200 may be incorporated into a lining of the jacket 300, such as within an inside pocket 310. For example the inside pocket can house a printed circuit board, a power source, a GPS chip, an RFID, chip and the one or more activity sensors. The components housed within the interior pocket 310 may have a casing that includes a USB port such that data and power can be transmitted and received to and from the portion of the fitness apparatus 200 incorporated into the jacket 300.

As noted herein above, the fitness apparatus 200 includes one or more user output devices 208 for providing auditory and/or visual feedback to a user. The one or more user output devices 208 are communicatively coupled to the one or more processors 202 over the communication path 204, such that the one or more processors 202 can control the various feedback provided over the one or more user output devices 208. For example, the one or more user output devices 208 may include one or more speakers and/or one or more displays. In some embodiments, the remote device 228 may be included as one of the one or more user output devices 208. The one or more user output devices 208 are configured to output information from the one or more processors 202 responsive to a command/request received from a user over the one or more user input devices 208.

In embodiments wherein the one or more user output devices 208 include a speaker 140, the speaker 140 is any device capable of transforming data signals from the one or more processors 202 into mechanical vibrations, in order to output audible information from the fitness apparatus 200. For example, in embodiments incorporating a speaker 140, the fitness apparatus 200 includes a voice audio chip, for producing a computerized voice output. The computerized voice can provide the user with a variety of information such as fitness data (e.g., heart rate, speed, pace, distance traveled, steps taken), turn-by-turn navigation, and the like upon a command or request from the user. In some embodiments, the speaker 140 can also output music.

Referring again to FIG. 2, a high decibel, waterproof speaker 140 is incorporated into the side of the shoe 100. Though the speaker 140 is shown as having a generally circular shape, it is contemplated the speaker 140 can have any polygonal or non-polygonal shape. The speaker 140 may be built into the sides of the shoe 100, back of the shoe 100, or the tongue portion 110 of the shoe 100. Accordingly, the location of the speaker 140 can be modified or changed to be located anywhere on the shoe 100. In some embodiments, and as illustrated in FIG. 4, the speaker 140 may be positioned behind vents 142 formed within the top portion 102 for an aerodynamic appearance. In some embodiments, the speaker 140 may be coupled to an amplifier to amplify the computerized voice output described above. As noted herein above, in some embodiments, speaker 140 may be a combined speaker 140/microphone device capable of both receiving voice commands and emitting auditory messages/sounds. In some embodiments, such as shown in FIG. 6, the speaker 140 may be incorporated with the sole portion 104 of the shoe 100. In particular, speaker 140 with or without an amplifier may be incorporated into the upper sole portion 116 or the inner sole 114 of the shoe 100 as shown.

Referring to FIG. 8, wherein at least a portion of the fitness apparatus 200 is incorporated into a jacket, one or more speakers 320 can be incorporated into the hood or collar. For example, a speaker 320 can be included on either side of the collar or hood to provide a user with surround sound. The speakers 320 can have amplifiers so music can be heard without a user having to wear headphones. The speakers 320 can be connected through cabling and wiring in the interior lining of the jacket 300 to other portions of the fitness apparatus 200 within the interior pocket 310.

Figure 9:
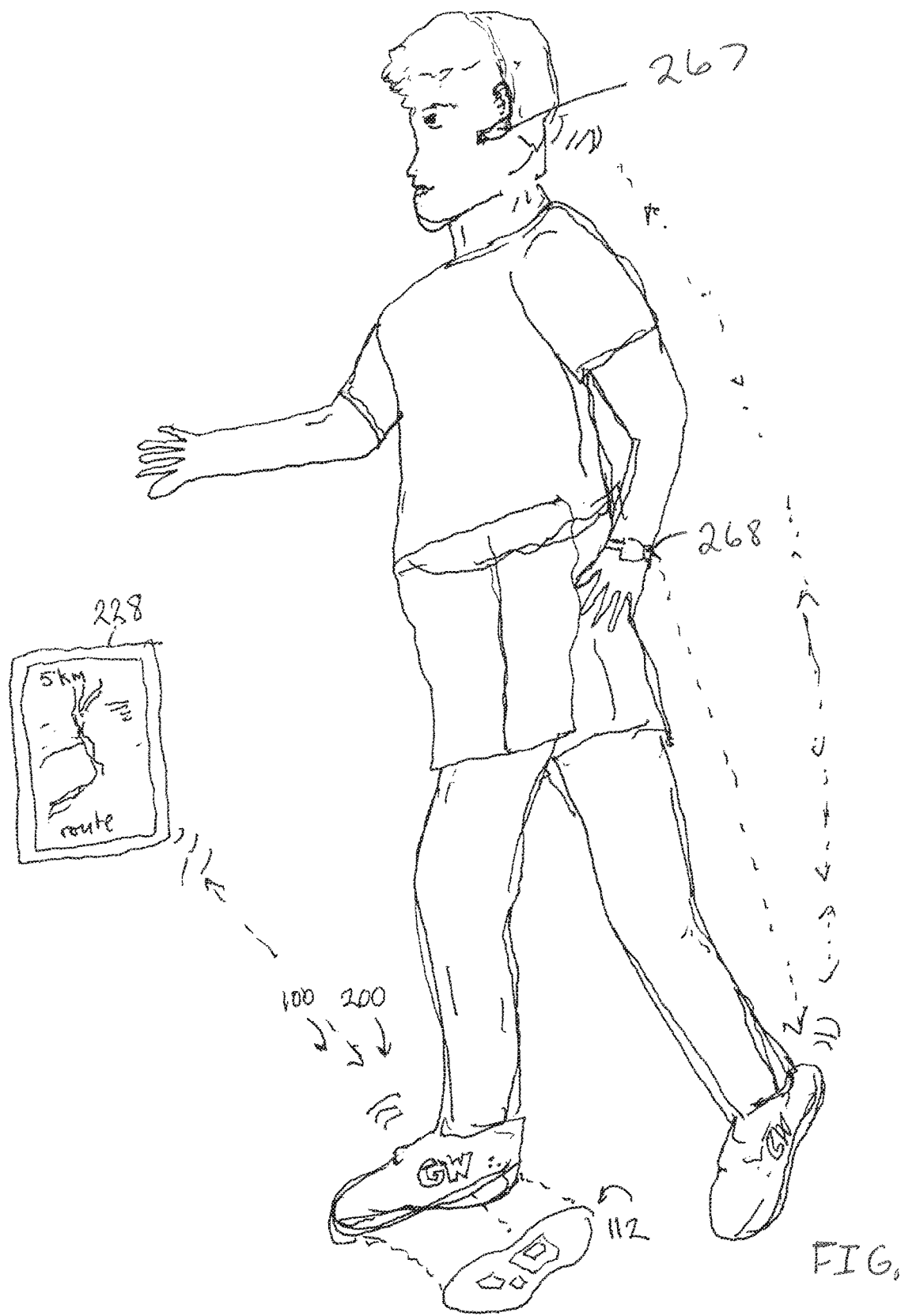
FIG. 9. illustrates the fitness apparatus of FIG. 2 on a user depicting how the worn fitness apparatus can communicate (transmit and receive data) with remote devices, smart watches, wireless ear buds, and/or (Bluetooth) headsets worn by the user.

In some embodiments, the one or more user output devices 208 may include a remote speaker 140, for example, a wireless headset 267, such as illustrated in FIG. 9 and worn by a user. Accordingly the wireless headset can be paired to the fitness apparatus 200 using the network interface hardware 218 (e.g., Bluetooth technology), such that output information from the fitness apparatus 200 can be sent over the network interface hardware 218 to the wireless headset 267. For example, the fitness apparatus 200 may wirelessly transfer music or turn-by-turn directions to the user's wireless headset.

It is noted, in some embodiments, the volume of the sound exiting the speaker 140 can be controlled through the one or more user input devices. In particular, the user could control volume with a voice command (e.g., "louder," "quieter"), through a dedicated volume button, or through an application on a remote device 228.

In embodiments wherein the one or more user output devices 208 include a display, the display is configured to provide visual output. For example, the display may display a logo, colors, music bars moving in sync to music, maps, fitness data (e.g., calories burned, distance traveled, steps taken, pace, heartrate, and the like), etc. The display may be any type of display that can be incorporated into a piece of apparel or accessory, such as a shoe 100, jacket 300, or the like. For example, the display may include any medium capable of transmitting an optical output such as, for example, a cathode ray tube, light emitting diodes, organic light emitting diodes, integrated component design piece, a liquid crystal display, a plasma display, or the like. In some embodiments, the display may utilize using LED-type technology such as OLED (organic light-emitting diode) technology and/or light thin-film digital display technology (LFG) which utilizes electro-luminescence (EL) wire in which a light film plate emits light in response to the passage of an electrical current. A light-film guide (LFG) display allows logos, patterns, designs, images, maps, and fitness data to be brightly illuminated. The display may be a seamlessly integrated component, i.e., stitched in the shoe. An OLED/LFG display can act like a dynamic billboard that can be programmed using the one or more user input devices 208 to change displays images, lights, patterns, dynamically. In some embodiments, the images displayed on the display could be programmed to change dynamically along to the beat of music. In some embodiments, the shoe 100 may have a dynamic mode in which the displayed images or the like are changed automatically like a screensaver. In some embodiments, the LFG display can have a regular mode wherein an illuminated logo 109 is displayed, such as shown in FIG. 4. In some embodiments, the display can be turned on or off using a voice command as described above.

Referring to FIG. 4, the shoe 100 is illustrated with an LFG display 150 seamlessly built into the side of the upper portion of the shoe 100. As noted above, though the display 150 is being referred to as an LFG display it could be any type of display including, but not limited to, LED and OLED. As illustrated, the LFG display 150 is presently programmed to display a logo 109 (e.g., GW) and the time (e.g., 8:22 PM). The LFG display 150 can show dynamically changing information including, but not limited to, time, speed, distance, other fitness data, logos, words, advertising, designs, patterns, music wave bars, frequency waves, maps, etc. For example, the LFG display 150 can pattern a kaleidoscope sky or clouds moving with colors morphing and changing. In some embodiments, the user can program, control, customize, and select images, text, designs, patterns, and other connect to be displayed using a mobile app. For example, a user may create their own content, including using their own images like a screen saver that is dynamically displaying, morphing, and/or rotating the images on the display using a mobile app or computer program.

Referring to FIG. 5, wiring for the LFG display 150 can run from printed circuit board 108 within the sole portion 104 through an inside wall of the top portion 102 between the top portion 102 and the interior portion 106 of the shoe 100. Wiring from the LFG display 150 may also run to a designated battery (e.g., power source 112 or 213) to provide power to the LFG display. A clear, durable, plastic (polymer) covering 152 can be provided over the LFG display 150 to protect the LFG display 150 from water and debris. It is contemplated that software downloaded to the fitness apparatus 200 from a smartphone application, as mentioned above, can provide new digital display designs and features. For example, downloaded software could cause frequency and music wave bars moves in sync to music on the LFG display 150 (similar to a synthesizer).

As noted herein, the fitness apparatus 200 may be incorporated in other articles besides shoes. Referring to FIG. 8, the fitness apparatus 200 is at least partially embedded in a jacket 300. In such embodiment, an LFG display 350 may be coupled to a sleeve of the jacket 300. As noted above, the printed circuit board 108 with the various electronic modules could be secured inside an inside pocket 310 in the apparel.

Still referring to FIG. 1, the fitness apparatus 200 includes the plurality of lighting elements 210. U.S. patent application Ser. No. 15/160,700, entitled "fitness apparatus 200," filed on May 20, 2016, which is hereby incorporated by reference in its entirety, describes lighting elements 210 incorporated into a shoe 100, other apparel, or accessory items that can be dynamically controlled by one or more processors 202. In the present disclosure, the plurality of lighting elements 210 are communicatively coupled to the one or more processors 202 and can be dynamically controlled by the one or more processors 202 based on instructions stored on the one or more memory modules 206 and/or received from the one or more user input devices 208. Referring also to FIGS. 2-5, the plurality of lighting elements 210 may be disposed on or in the shoe 100, or apparel, such as a track suit warm-up jacket 300 (shown in FIG. 8 with lighting elements 308 on arms and shoulders) or pants, or other article or accessory (e.g., handbag, backpack, and the like). In embodiments where the fitness apparatus 200 is embedded in the shoe 100, the plurality of lighting elements 210 may be placed in and/or on the sole portion 104 and/or the top portion 102 of the shoe 100.

At least some of the plurality of lighting elements 210 may be disposed toward the front of the shoe 100 (e.g., the tongue portion 110 of the shoe 100 or at a toe 115 of the shoe 100) for illumination of an area directly in front of the shoe 100. Such front lighting element 211 may be provided as an LED strip, for example. The front lighting element 211 may be coupled to the top portion 102, as shown, or to the sole portion 104. In some embodiments, the forward lighting element 211 may include high watt/lumen white lights to provide individuals with adequate lighting such that they can see a path in front of them in dimly lit places or at night to avoid various obstacles (e.g. pot holes, debris, and other impediments that one could trip over). The front lighting element 211 essentially acts as a "flood" light with a wide angle of reflection/incident directly in front of the shoe 101. In some embodiments, a clear plastic waterproof covering may be disposed over the front lighting element 211 to protect the front lighting element 211 from water and/or debris. In some embodiments, included as one of the one or more user input devices 208, is a lighting power switch 110 that is integrated into the top portion 102 of the shoe 100 (e.g., the tongue portion 110 or the sides of the top portion 102) that allow a user to manually activate the front lighting element 211.

In some embodiments, additional lighting elements 210 may be provided around the perimeter of the sole portion 104 or on the upper portion. In some embodiments, the sole portion 104 of the shoe 100 may be transparent or translucent such that the plurality of lighting elements 210 are visible through the sole portion 104 of the shoe 100. For example, LED strips can be imbedded around the perimeter of the sole of the shoe 100.

In yet further embodiments, at least some of the one or more lighting elements 210 may utilize LED-type technology such as OLED or light thin-film guide technology (LFG) which utilizes electro-luminescence (EL) wire in which a light film plate emits light in response to the passage of an electrical current. The EL film produces single-frequency (monochromatic) light that has very narrow bandwidth, is uniform, and is visible from a great distance. For example, the top portion 102 of the shoe 100 can include one or more LED-type displays or light film guides 130 as illustrated in FIG. 2. For example, FIG. 2 illustrates a first light film guide 132, second light film guide 134, and a third light film guide 136 provided in a swooping pattern. The one or more light film guides 130 may be disposed beneath a surface 103 of the top portion 102 of the shoe 100. One or more windows 105 formed within the surface 103 of the top portion 102 visibly expose the one or more light film guides 130. In some embodiments, there may only be one light film guide 130 positioned beneath a surface 103 of the top portion 102 of the shoe 100, wherein various windows 105 visibly expose desired portions of the light film guide. The one or more windows 105 may be provided in any desired shape, size, pattern, or number. A clear plastic waterproof covering may be disposed over the visible portions of the one or more LED-type displays and/or light film guides 130 to protect the one or more LED-type displays and/or light film guides 130 from water and/or debris. As will be described in greater detail herein, the one or more lighting elements 210 may be programmed to move in sync and/or dynamically changed to the beat of music.

In some embodiments, the at least one logo 109 itself may be made of one or more of lighting elements 210. In embodiments, the logo 109 may be made of the plurality of lighting elements 210 and may be detachable. In embodiments, the plurality of lighting elements 210 may be LED lights, electroluminescence (EL) lights, incandescent lights, HID lights, fluorescent lights, halogen lights or the like. In some embodiments, the plurality of lighting elements 210 can display between about 20 to about 30 different colors. In some embodiments, the plurality of lighting elements 210 can be controlled by the one or more processors 202 to display a light show and may be controlled/programmed by the user, i.e., via a mobile app. In some embodiments, the at least on logo 109 is replaced with the LFG display 150 discussed above.

Still referring to FIG. 2, machine readable instructions stored in the one or more memory modules 206 cause the fitness apparatus 200 to activate the plurality of lighting elements 210 in a lighting mode when executed by the one or more processors 202. The lighting mode of the plurality of lighting elements 210 is the frequency with which the plurality of lighting elements 210 emit light. As used herein, the lighting mode refers to a pre-determined pattern and/or color emitted by the plurality of lighting elements 210. In embodiments, various lighting modes may be stored in the one or more memory modules 206 and executed by the one or more processors 202. Examples of lighting modes include, but are not limited to strobe lighting, blinking lighting, static lighting, fading lighting, or a combination thereof. In some embodiments, the lighting modes may be activated automatically by the one or more processors 202 to dynamically change during use. In some embodiment, a voice command can change the lighting mode. In one lighting mode, one or more lighting elements 210 embedded around the perimeter of the sole portion 104 of the shoe 100 can be programmed to be animated such that a light or lights appear to zip around the sole portion 104. The various lighting modes can be combined in various ways to provide a light show display.

In some embodiments, other types of lighting modes may be designed or programmed by the user such as a mode to sync the lighting elements 210 to music or rhythms (or to change the static color as various running distances are reached.) In such an embodiment, the shoe 100 speaker 140 described above may process/amplify music and sound stored in the one or more memory modules 206, or otherwise available to the fitness apparatus 200 (e.g., from a remote device 228), and provide a signal of the detected vibrations to the one or more processors 202 which can be converted into light movements. In one embodiment, the colors of the plurality of lighting elements 210 could change to the beat of the sound. In some embodiments, and as disclosed in U.S. patent application Ser. No. 15/160,700, machine readable instructions stored in the one or more memory modules 206 cause the fitness apparatus 200 to activate the plurality of lighting elements 210 to display a pre-selected lighting mode in response to obtaining a pre-selected fitness goal (e.g., distance achieved, calories burned, and the like) when executed by the one or more processors 202.

In yet further embodiments, the one or more lighting elements 210 include a power indicator light e.g. power bar indicators (not shown) that indicates the remaining amount of power (e.g., battery life) left in the fitness apparatus 200. For example, machine readable instructions stored on the one or more memory modules 206 and executed by the one or more processors 202 may cause the power indicator light to blink red while the fitness apparatus 200 is recharging and turn solid green or stop blinking when the fitness apparatus 200 is fully charged.

Referring to FIG. 3, the one or more user input devices 208 include a lighting power switch 120. The lighting power switch 120 is configured to control at least some of the plurality of lighting elements 210. In particular the light power switch 120 may control turning on and off the front facing lighting element on the shoe 100. Accordingly, in some embodiments, the lighting power switch 120 may be a button that can be clicked using the user's hands, and may be positioned in an accessible location. In embodiments, the lighting power switch 120 is disposed on the shoe 100 (e.g., the tongue portion 110, as shown in FIG. 3, or sides of the shoe 100). In other embodiments where the fitness apparatus 200 is integrated into other apparel, such as a jacket 300, or gear, such as a handbag, the lighting power switch 120 may be disposed within the interior portion of the jacket 300 or handbag. Further, in some embodiments, a lighting power switch 120 may not be provided, and the plurality of lighting elements 210 may be turned on, turned off, dimmed or controlled in other ways such as, for example, input on a remote device 228 an app or program or a voice command as described herein. Additional features for the lighting power switch 110 are described in U.S. patent application Ser. No. 15/160,700.

Referring again to FIG. 1, the fitness apparatus 200 also includes a light sensor 216. In embodiments, the light sensor 216 is communicatively coupled to the one or more processors 202. The light sensor 216 may be an analog light sensor 216. In some embodiments, non-limiting examples of light sensor 216 include photocells, light-dependent resistors, or photoresistors. The machine readable instructions stored in the one or more memory modules 206 cause the fitness apparatus 200 to activate the plurality of lighting elements 210 to automatically turn on in response to a dark external environment based on a determination by the light sensor 216 when executed by the one or more processors 202. In embodiments, the light sensor 216 is disposed on the exterior portion of the shoe 100. The light sensor 216 detects the amount of light present in an external environment. When light is insufficiently present, the fitness apparatus 200 is configured to automatically turn on the plurality of lighting elements 210. For example, when a user is running outside and the light sensor 216 detects a change in the amount of light in the external environment, i.e. the environment surrounding and outside of the shoe 100, the one or more processors 202 is configured to automatically turn on the plurality of lighting elements 210. Similarly, when the light sensor 216 determines the presence of light in the external environment, the one or more processors 202 may be configured to automatically turn off the plurality of lighting elements 210. In some embodiments, the fitness apparatus 200 may not include a light sensor 216.

Still referring to FIG. 2, the fitness apparatus 200 includes one or more activity sensors 230. The one or more activity sensors 230 can include various sensors that monitor the activity of the user. In some embodiments, the GPS chip 214 can use location information to determine certain fitness information such, for example, distance traveled. Accordingly the GPS chip 214 may be included as one of the one or more activity sensors 230. Other activity sensors 230 can include but are not limited to, an accelerometer, speed sensors, heart rate sensors, blood pressure sensors, temperature sensors, pressure sensors 264, tilt sensors, and other motion sensors.

Referring to FIGS. 6 and 7 the various activity sensors 230 can be disposed within the sole portion 104 including, but not limited to, the inner sole portion 114 and the lower sole portion 104. Such location of sensors may allow the activity sensors 230 to more accurately reflect activity of the user as the sensors would be directly beneath a user's foot. For example the inner sole 114, which is removable, may contain several of the components described herein. For example, the inner sole 114 can include a circuit board having embedded components such as a rechargeable battery, accelerometer, pressure sensors 264, a voice/audio chip 217, motion sensors, WiFI Chip, other network interface hardware 218, and a USB port 250 for recharging. Several of the components may also be placed in a cavity in the bottom sole 112 such as a printed circuit board 108, one or more processors 202, a battery, GPS chip 214, and network interface hardware 218. The components located on the inner sole 114 may be communicatively coupled with the components located in the bottom sole 112. Using the one or more activity sensors 230, each movement of a user's foot can be detected and measured. As discussed above, the information detected by the one or more activity sensors 230 can be outputted through the one or more user output devices 208 (e.g., the speaker 140, display, or remote device 228)

In some embodiments, it is contemplated that based on the biomechanical data measured by the one or more activity sensors 230, the one or more processors 202, executing training software stored on the one or more memory modules 206 or available over the network interface hardware 218 from a remote device 228 running, the fitness apparatus 200 can provide real-time audio training, feedback, and profiles of activity performance (e.g., running, cycling, and the like). The audio feedback can be provided through a speaker 140 provided on the shoe 100 or can be provided to wireless ear buds or headset. Memory stored on the one or more processors can analyze motion and cadence to sense individual stride and pace. Essentially, the fitness apparatus 200 can be an athlete's kinematic running guide and can analyze speed zones, running economy, cadence efficiency, calorie expenditure and the like, and provide such information to the user through the one or more user output devices 208 or through a mobile app on a remote device 228. For example, the fitness apparatus may provide helpful feedback such as "slow down," "run faster," "you have burned 100 calories," etc. In some embodiments, the fitness apparatus 200 can have a triathlon mode. For example, if an athlete was doing a triathlon, the fitness apparatus could track distance and calories separately for running and cycling. The cycling mode could include pedaling tracking and pedal revolutions per minute which would not be included in a running mode. As noted herein, real-time feedback regarding the athlete's performance could be provided over the one or more user output devices 209.

As noted herein, the fitness apparatus 200 may be incorporated across several articles including a jacket 300 such as shown in FIG. 8. For example, the jacket 300 could be part of a track warm up suit, fleece, half zip, windbreaker, and the like. The one or more activity sensors 230 may be incorporated in various locations on the jacket. For example, a belt 320 may be incorporated within the jacket 300 to strap the one or more activity sensors 230 to the body of the user (e.g., around a user's midsection). For example, a heartrate monitor could be strapped to the user's body to measure the user's heartrate during various activities. In some embodiments, the one or more activity sensors 230 can be snapped into button holes on the jacket 300 or other apparel and then connected to the belt 320. In other embodiments, the one or more activity sensors could be securely placed within an inside pocket 310 of the jacket 300. It is contemplated that the material of the apparel is waterproof or water resistance to protect the components of the fitness apparatus. In some embodiments, the one or more activity sensors 230, or even all components of the fitness apparatus 200 can be disconnected from the jacket 300 (or other apparel) for washing and then reinserted.

In embodiments wherein the one or more activity sensors 230 include tilt sensors, the tilt sensors may be coupled to the arm(s) of the jacket 300, and output a signal indicative of the arms of the jacket 300 moving. Accordingly the one or more processors 202 can execute logic stored on the one or more memory modules 206 to determine that the arms of the jacket 300 are moving based on the output of the tilt sensor. In some embodiments, it is contemplated that the lights 308 coupled to the jacket 300, such as those on integrated thin light strips (that may be detachable from the jacket through zippers or buttons), only illuminate when the arms are moved to preserve power.

The various activity sensors 230 may be configured, in combination or on their own, to determine fitness data such as calories burned, distance between the start position and the end position, average speed of the user while traversing from the start position to the end position, the speed traveled, heart rate, and the like. In some embodiments, the one or more activity sensors 230 are configured to determine cadence or revolutions per minute, when the fitness apparatus 200 is being used for cycling activities. In some embodiments, biomechanical information captured by the one or more activity sensors 230 is used to determine cadence stride, leaping and sprinting. In embodiments, fitness data may be computed using machine readable instructions stored in the one or more memory modules 206 and executed by the one or more processors 202. As noted above, the fitness data can be wirelessly transferred from the fitness apparatus 200 to a remove server 254, 256 or a remote device 228. Additionally, the one or more activity sensors 230 may also be configured to measure the number of steps taken, activity intensity, speed of movement such as running or cycling, and metrics related to average and maximum speed or acceleration between the start position and the end position. In embodiments, the fitness data may be displayed on the LED-type/LFG display 150 or transmitted to a remote device 228 via network interface hardware 218 such as the RFID chip, the Bluetooth® chip, WiFi chip, or a combination thereof, supporting wireless and GSM network 222 data communications such as general packet radio system (GPRS). The one or more activity sensors 230 in the shoe 100 will give more accurate data readings than in watches because they measure actual cadence of the foot.

Referring to FIG. 1, the fitness apparatus 200 includes a first power supply 212. The first power supply 212 is configured to provide power to the plurality of lighting elements 210 and other components of the fitness apparatus 200. The first power supply 212 may be a battery. In some embodiments, the first power supply 212 may be a rechargeable battery. In some embodiments, the battery is a lithium battery that supplies power to the different components of the fitness apparatus 200. In some embodiments, there may be a second or redundant battery or second power supply 213. For example, the second power supply 213 can supply power to the fitness apparatus 200 when the power supply 212 is drained of power. In some embodiments, the second power supply 213 can instead, be a dedicated power supply 212 to one or more modules within the fitness apparatus 200. For example, the second power supply 213 may be a dedicated power supply 212 for the GPS chip 214, WiFi chip, front lighting element 211, the one or more user output devices 208, and the like.

Referring to FIG. 5, both the first power supply 212 and the second power supply 213 are illustrated as embedded within the sole portion 104 of the shoe 100. Referring to FIG. 6, in some embodiments, one of the first and second power supplies 212, 213 may be embedded in the inner sole 114 and the other of the first and second power supplies 212 may be embedded in the bottom sole 112. As noted herein above, when the power available for the fitness apparatus 200 is low, the indicator light might provide information to a user that the device needs to be charged. In some embodiments, it is contemplated that when the power available for the fitness apparatus 200 is low the LFG display 150 may display a warning and/or computerized speech output by the speaker 140 may indicate that power is low.

Still referring to FIG. 1, the fitness apparatus 200 also includes a charging port 224. The charging port 224 is communicatively coupled to the one or more processors 202 and the power supply 212 which may include the first power supply 212 and a second (redundant) power supply 213. In embodiments, the charging port 224 may be placed in the interior portion 106 of the shoe 100 (between the interior lining and shoe 100 exterior of the top portion 102, see FIGS. 3 and 5) or the tongue portion 110 of the shoe 100. In embodiments where the fitness apparatus 200 is embedded in other apparel, the charging port 224 may be placed on an interior or exterior portion of apparel, such as a jacket 300 or pants, or accessories (e.g., handbags, backpacks, and the like). In embodiments, the charging port 224 may be a USB charging port 224. In some embodiments, the inner sole portion 114 includes a battery that may be wirelessly charged. In some embodiments, the inner sole portion 114 includes a battery that may be wirelessly charged by removing the inner sole from the shoe and placing the inner sole on a wireless charging mat. For example, referring to FIG. 6, it is contemplated the inner sole portion 114 includes power supply 213. The inner sole portion 114 may be removable and configured for wireless charging, e.g. induction charging, wherein the inner sole portion 114 can be laid on an induction charging mat to charge the fitness apparatus 200. In some embodiments, the charging port 224 may be located in the bottom sole 112, such that when charging a power supply 212 in the bottom sole 112, the power supply 213 in the inner sole is recharged by the power supply 212 in the bottom sole 112 when the inner sole 114 is connected to the bottom sole 112.

Referring again to FIG. 1, the fitness apparatus 200 also includes one or more temperature sensors 242 communicatively coupled to the one or more processors for outputting a signal indicative of the temperature of the user and/or the environment of the user. As will be described below, when a temperature of the user or the environment of the user falls below a predetermined value one or more heating elements can be activated to warm the user. Such embodiments are particularly applicable to a fitness apparatus as incorporated into a garment such as the jacket 300. Referring to FIG. 8, the one or more temperature sensors 242 may be incorporated in to the arms or sleeves of the jacket 300 and/or in pants (not shown). As noted above it is also contemplated that a microphone and/or speaker communicatively coupled to a processor and circuit board could be integrated into the jacket 300. Computerized voice information, such as navigation instructions, or music could be output through such speakers. Information and instructions could be spoken into the microphone (e.g. integrated into the jacket collar or arm) that could, in turn, be used to communicate with the shoe 100 in FIG. 2 or remote devices or other devices worn by the user such as a wireless ear buds, Bluetooth headset 267 and/or smartwatch 268 shown in FIG. 9.

Referring again to FIG. 1, the fitness apparatus 200 also includes one or more heating elements 240. The one or more heating elements 240 are coupled to the communication path 204 such that the communication path 204 communicatively couples the one or more heating elements 240 to other modules of the fitness apparatus 200. The one or more heating elements 240 are configured to produce thermal feedback in response to a low temperature reading from the one or more temperature sensors 242. Non-limiting examples of heating elements 240 include resistors, conductive plates, heating pads, and heat fans. In some embodiments, the fitness apparatus 200 may comprise combination of heating elements 240. Referring again to the jacket 300 of FIG. 8, the one or more heating elements 240 can be incorporated in to the arms or sleeves such that the one or more heating elements 240 can warm the sleeves and inside lining of the jacket 300 thereby providing warmth in cold temperatures. In yet further embodiments, the one or more heating elements could be inserted into the lining of track warm-up suit pants, cycling pants, running tights, and the like. The one or more heating elements can be automatically activated or activated by the one or more user input devices 208 including by voice, a dedicated button, from a remote device 228, etc. Information related to the use of the one or more heating elements 240 and the data from the one or more heat sensors 242 can be stored on the one or more memory modules or communicated to a remote device as described above.

Referring again to FIG. 1, the fitness apparatus 200 can include one or more pressure sensors 264. As noted above, the one or more pressure sensors 264 may be included as the one or more activity sensors 230. A pressure signal output by the one or more pressure sensors 264 is indicative of a pressure applied by a user's foot to the sole portion 204. The pressure signal can be provided to the one or more processors 202, and may allow the one or more processors 202 to dynamically adjust the cushioning within the sole portion 104 of the shoe 100 with the pneumatic adjustment system 260 incorporated into the bottom sole portion 104 of the shoe 100. Referring also to FIG. 7, the one or more pressure sensors 264 can be incorporated into the inner sole 264 at various locations to measure the pressure exerted by a user's foot at a discreet locations within the sole portion 104 of the shoe 100.

As noted above, the fitness apparatus also includes a pneumatic adjustment system 260 communicatively coupled to the one or more processors. The pneumatic adjustment system 260 is embedded within the bottom sole portion 112 and includes a pneumatic electric motor 262 and pneumatic springs 266 operatively coupled to the pneumatic electric motor 262 whereby operation of the pneumatic electric motor 262 causes the pneumatic springs 266 to expand or contract to modify the cushioning provided by the sole portion 104. The pneumatic electric motor 266 may be configured to provide compressed air to the pneumatic springs 266 through a manifold (not shown) controlled by the one or more processors such that each pneumatic spring 266 is individually adjustable. Accordingly the pneumatic springs 266 can be individual controlled to cause the inner sole 114 to automatically adjust by raising, lowering, and tilting the portions of the inner sole 214.

In operation, the one or more processors 202 receive a pressure signals from the one or more pressure sensors 264.

The one or more processors can cause the fitness apparatus 200 to calculate a cushioning adjustment and adjust the amount of air in the pneumatic springs 266 with the pneumatic electric motor 266 so as to facilitate advanced cushioning and foot support as a user moves. As with other features described herein, the pneumatic adjustment system 260 can be controlled using the one or more user input devices 208 (e.g., voice control, a remote device 288, etc.)

Referring again to FIG. 8, it has been noted that the fitness apparatus 200 may be incorporated across several pieces of apparel. For example a portion of the fitness apparatus 200 may be incorporated into the jacket 300 and another portion of the fitness apparatus 200 may be incorporated into a shoe 100. Or each article may comprise its one independent fitness apparatus wherein each apparatus can be paired to one another using any communication method as described herein (e.g., Bluetooth technology).

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A shoe comprising:
   top portion configured to provide covering to a top of a user's foot;
   a sole portion coupled to the top portion;
   one or more processors embedded within the sole portion;
   one or more pressure sensors communicatively coupled to the one or more processors and configured to output a pressure signal indicative of pressure applied by the user's foot to a portion of the sole portion;
   a pneumatic adjustment system operable to adjust a cushioning of the sole portion; one or more memory modules communicatively coupled to the one or more processors;
   machine readable instructions stored in the one or more memory modules that, when executed by the one or more processors, cause the shoe
      to determine a pressure applied by the user's foot to the portion of the sole portion based on the pressure signal from the one or more pressure sensors;
      to calculate a cushioning adjustment;
      to adjust the cushioning of the sole portion with the pneumatic adjustment system;
   one or more user input devices communicatively coupled to the one or more processors,
   wherein the one or more user input devices comprise at least a microphone;
   a user output device communicatively coupled to the one or more processors; and
   machine readable instructions stored in the one or more memory modules that when executed by the one or more processors, cause the shoe
      to receive a command from a user with the one or more user input devices;
      to process the command from the user and to output information with the user output device relevant to the command from the user.

2. The shoe of claim 1, wherein the sole portion comprises an inner sole and an bottom sole wherein the inner sole sits on top of the bottom sole.

3. The shoe of claim 2, wherein the one or more pressure sensors are coupled to the inner sole and the pneumatic adjustment system coupled to the bottom sole at a position below the inner sole.

4. The shoe of claim 1, wherein the machine readable instructions, when executed by the one or more processors, cause the shoe to dynamically adjust the cushioning of the sole portion with the pneumatic adjustment system throughout a use session of the shoe.

5. The shoe of claim 1, wherein the pneumatic adjustment system comprises a motor and a pneumatic spring operatively coupled to the pneumatic spring, wherein the motor is operable to supply compressed air to the pneumatic spring.

6. The shoe of claim 1, wherein the user output device comprises a speaker coupled to at least one of the top portion and the sole portion.

7. The shoe of claim 1, further comprising a GPS chip, wherein information relevant to the command includes navigation instructions.

8. The shoe of claim 1, further comprising network interface hardware communicatively coupled to the one or more processors, wherein the network interface hardware is configured to communicatively couple the one or more processors to a remote speaker.

\* \* \* \* \*